Figure 1:
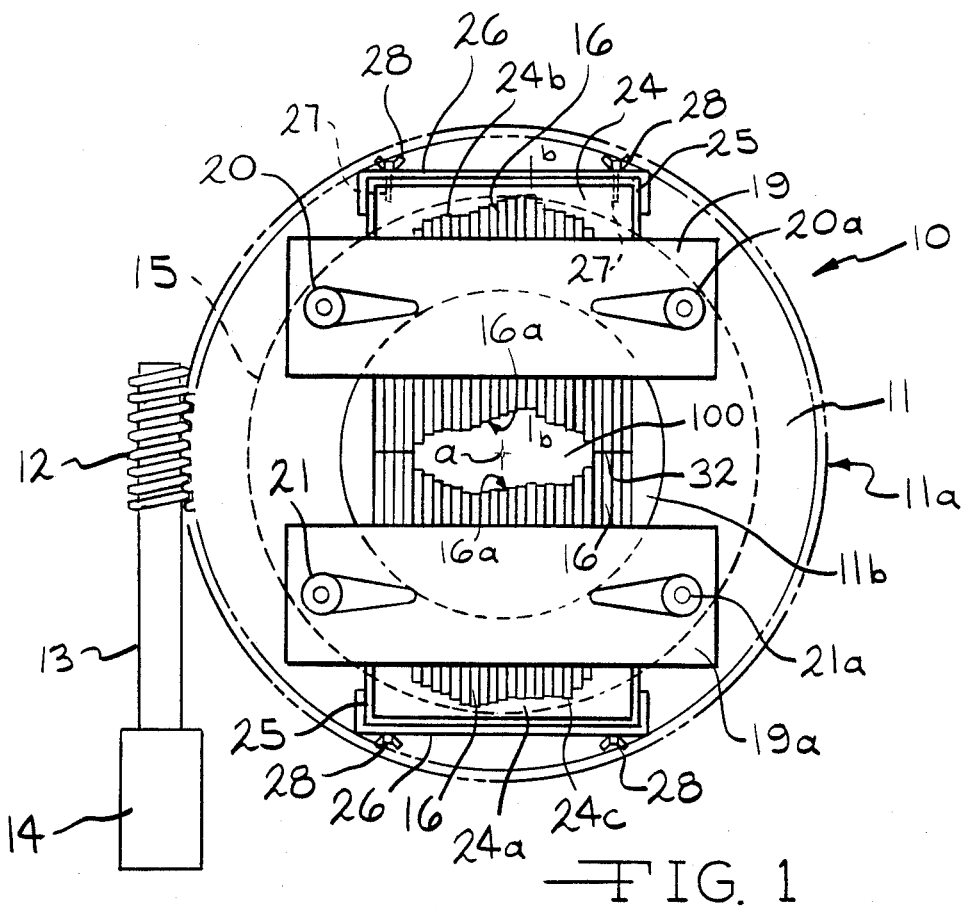

United States Patent [19]

Maughan et al.

[11] Patent Number: 4,754,147
[45] Date of Patent: Jun. 28, 1988

[54] VARIABLE RADIATION COLLIMATOR

[75] Inventors: Richard L. Maughan, Grosse Pointe Park; Gabe F. Blosser, Haslett; Emanuel B. Jemison, Lansing; Henry G. Blosser, East Lansing, all of Mich.

[73] Assignee: Michigan State University, East Lansing, Mich.

[21] Appl. No.: 850,486

[22] Filed: Apr. 11, 1986

[51] Int. Cl.[4] .............................................. G21K 1/04
[52] U.S. Cl. .................................. 250/505.1; 250/251; 378/150; 378/152
[58] Field of Search ............................. 250/505.1, 251; 378/150, 152

[56] References Cited

U.S. PATENT DOCUMENTS 3,543,384 12/1970 Hansen .............................. 250/505.1
4,463,266 7/1984 Brahme ............................. 250/505.1
4,507,616 3/1985 Blosser et al. ..................... 250/492.3
4,534,052 8/1985 Milcamps ............................. 378/152

FOREIGN PATENT DOCUMENTS 0192300 11/1907 Fed. Rep. of Germany ...... 378/150

Primary Examiner—Craig E. Church
Assistant Examiner—Jack I. Berman
Attorney, Agent, or Firm—Ian C. McLeod

[57] ABSTRACT

A variable collimator 10 for shaping the cross-section of the beam 100 is described. The collimator relies upon rods 16 which are positioned around the beam axis a-a with the rod 16 axis b-b perpendicular to the beam axis. The rods are shaped by shaping member 24 which is cut to the shape of an area of a patient or other surface to be irradiated.

26 Claims, 3 Drawing Sheets

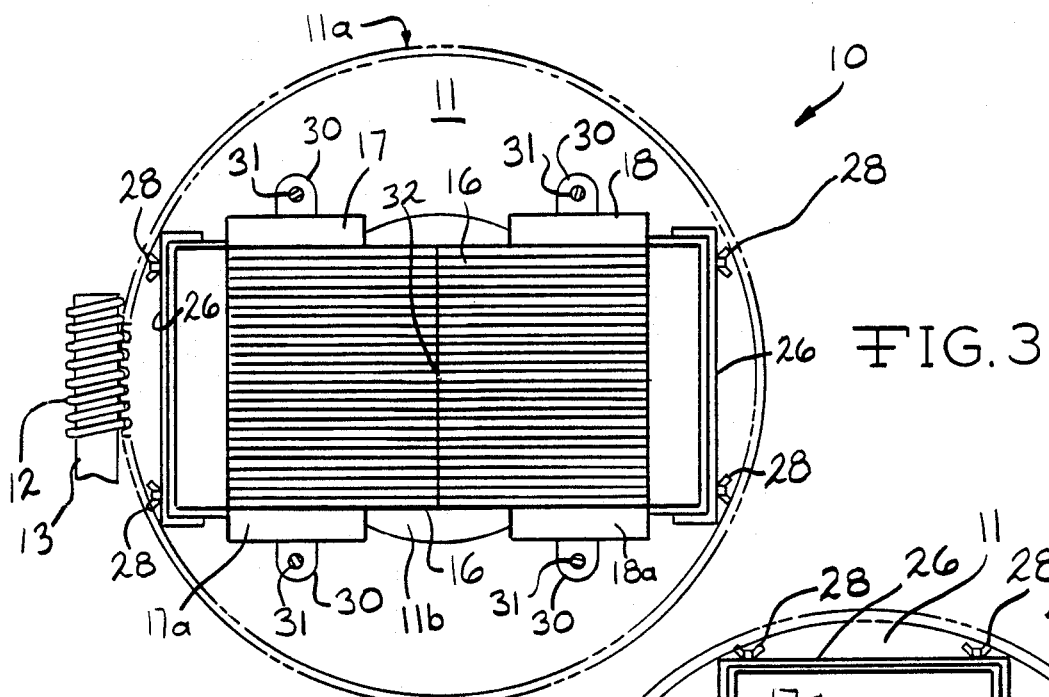
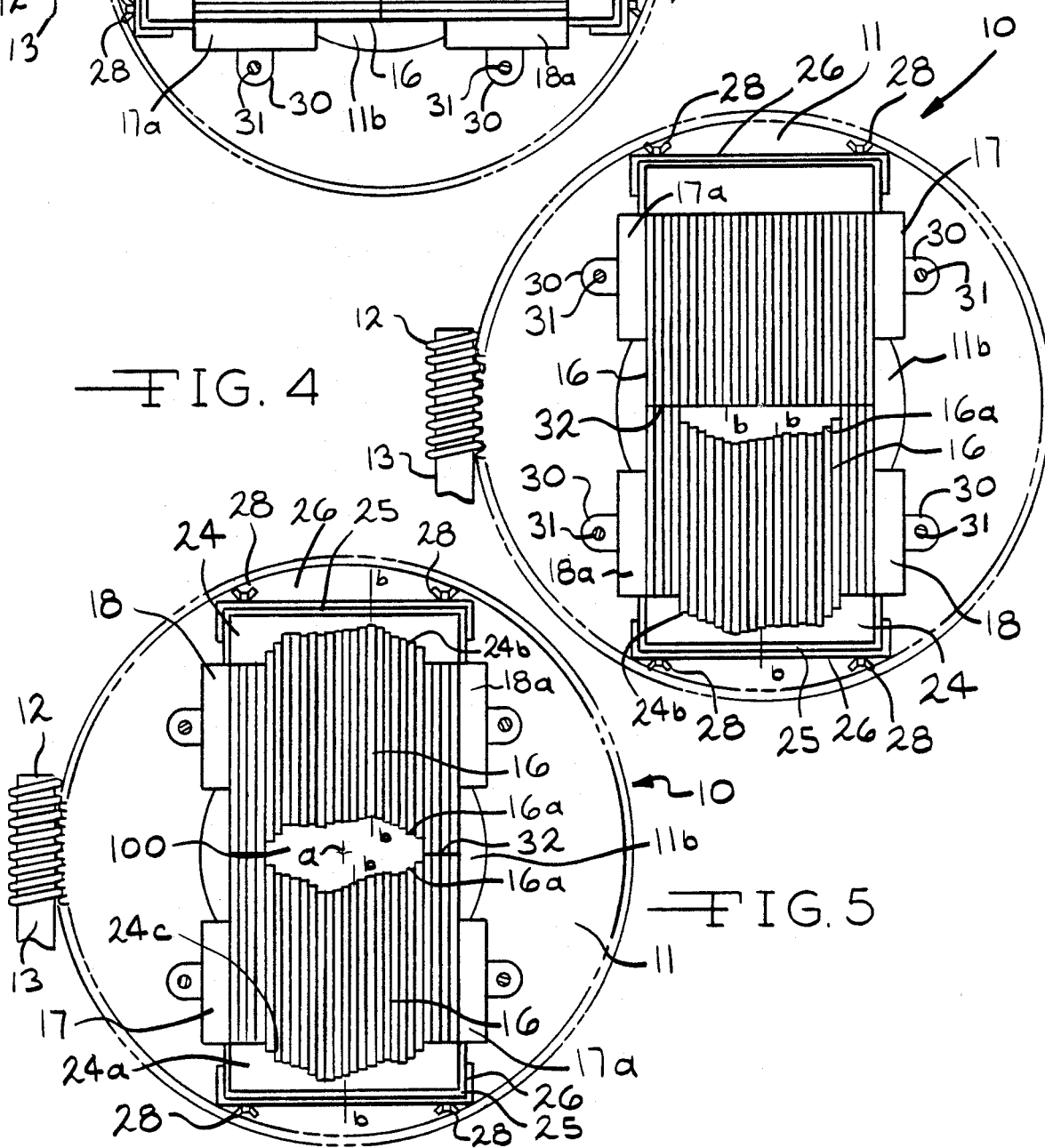
FIG. 3
FIG. 4
FIG. 5

4,754,147

VARIABLE RADIATION COLLIMATOR

BACKGROUND OF THE INVENTION

(1) Field of the Invention

The present invention relates to a collimator for a beam of radiation which allows rapid adjustment of the cross-section of the beam for different patients or other surfaces to be irradiated. In particular, the present invention uses bundles of adjustable clamped rods to shape the cross-section of the beam.

(2) Prior Art

Collimator devices for radiation are well known to the prior art. Most of them provide beams with a fixed cross-section. The problem is that this configuration is cumbersome where the cross-section of the beam has to be changed such as in patient treatment with the radiation in a defined area of the body.

Variable collimator devices are also well known to the prior art. These devices provide an interfering member in the beam. U.S. Pat. No. 4,463,266 to Brahme describes a collimator which uses wedge shaped slabs mounted on an arcuate surface which moves into the beam so as to define the beam. This device is complicated and expensive to build because of the precision of the fit of the wedges relative to each other. Other prior art includes camera or iris type lenses which uniformly change the diameter beam and thus are not suitable where the beam is to have an irregular cross-section. One prior art example is U.S. Pat. No. 4,534,052 to Milcamps. None of this prior art provides a means for rapidly and simply adjusting the beam cross-section non-uniformly.

OBJECTS

It is therefore an object of the present invention to provide a variable radiation collimator which allows for rapid and non-uniform adjustment of the beam cross-section, particularly from patient to patient. Further it is an object of the present invention to provide a collimator which is inexpensive to construct and operate to vary the beam cross-section. These and other objects will become increasingly apparent by reference to the following description and the drawings.

IN THE DRAWINGS

FIG. 1 is a front view of the variable collimator 10 of the present invention particularly showing two opposed sets of multiple rods 16 in bundles with ends 16a facing each other to define the beam 100 cross section.

Figure 2:
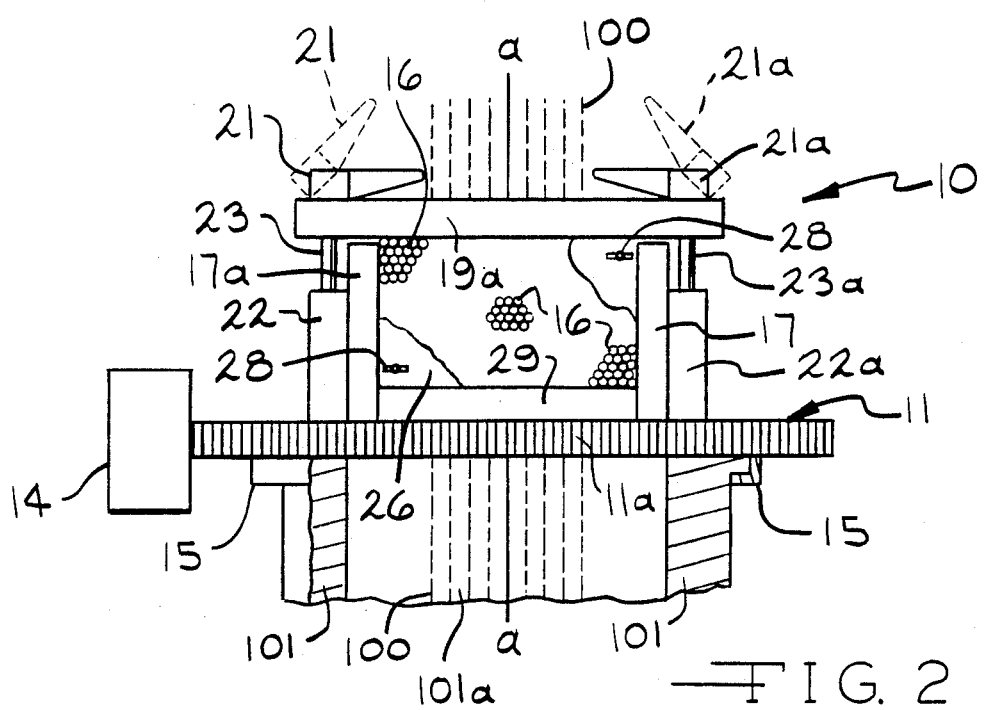

FIG. 2 is a side view of FIG. 1 in partial section particularly showing the clamps 21 and 21a for the rods 16.

FIGS. 3 to 5 are front views of the collimator shown in FIG. 1 showing the steps in the positioning of the rods 16 to define the beam 100 cross-section by means of gravity due to rotation of the support plate 11 by ring gear 11a and worm gear 12.

Figure 6:
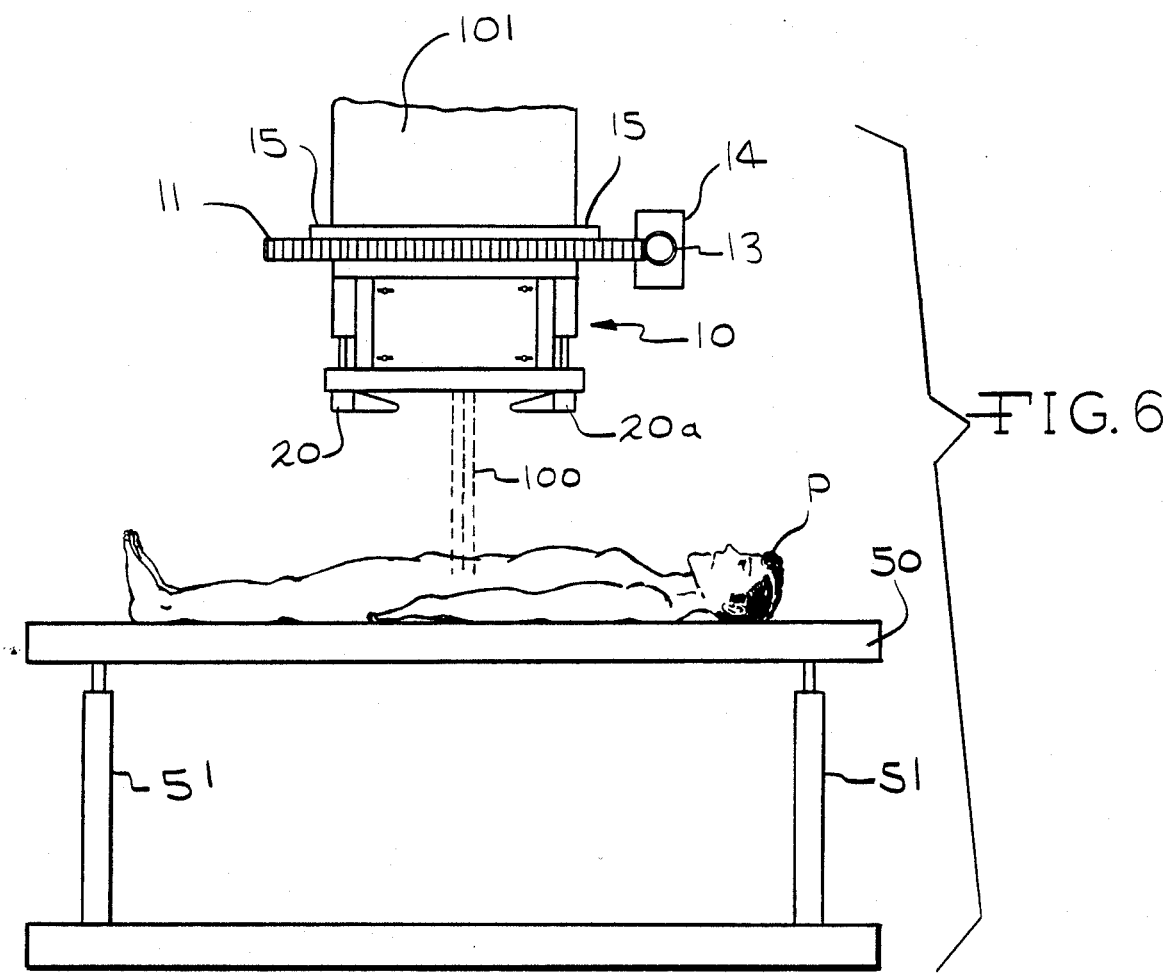

FIG. 6 is a perspective view of the variable radiation collimator of the present invention, particularly illustrating a table 50 with legs 51 for positioning a patient's body P horizontally and perpendicular to beam 100 and also illustrating the support plate 11 mounted on a cyclotron 101 (or accelerator or other radiation source) by mounting bearing 15.

Figure 7:
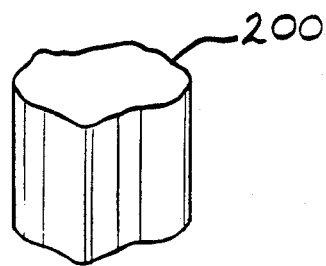

FIG. 7 shows a pattern 200 for defining the shape of the beam 100 such as shown in FIG. 1.

GENERAL DESCRIPTION

The present invention further particularly relates to a collimator apparatus for producing a cross-sectionally shaped beam of radiation from a radiation source which comprises: support plate means having a central opening around a beam axis through which the beam of radiation can pass; a bundle of nested metal rods mounted on the support plate means, each rod having a longitudinal axis perpendicular to the beam axis and having first ends which together define a first surface for shaping the beam around the beam axis and opposite ends from the first ends; a holder means for positioning a rod shaping means adjacent the opposite ends of the rods, wherein the rod shaping means has a second surface corresponding to the first surface which defines varying positions of the first ends of the rods so that the first surface is defined and the beam is shaped by the first ends of the rods; and clamping means mounted on the support plate means for securing the rods together in the shape defined by the shaping means.

The present invention also relates to a method of producing a cross-sectionally shaped beam of radiation from a radiation source which comprises: providing a collimator apparatus for producing a cross-sectionally shaped beam of radiation from a radiation source which comprises: support plate means having a central opening around a beam axis through which the beam of radiation can pass; a bundle of nested rods mounted on the support plate means each rod being movable into the beam at an angle to the beam axis to interfere with the beam, the rods having first ends which together define a first surface for shaping the beam around the beam axis and opposite ends from the first ends of the rods; a holder means mounting the rods so that the first surface is defined and the beam is shaped by the first ends of the rods; and releasable clamping means mounted on the support plate means and engaging the rods between the first and second ends to secure the rods together in the shape defined by the first ends of the rods; mounting the rod shaping means in the holder means to thereby define the first surface for shaping the beam in the collimator; clamping the rods with the clamping means; and irradiating the defined area of an object with the shaped beam defined by the rods.

The present invention finally particularly relates to a method of producing a cross-sectionally shaped beam of radiation from a radiation source which comprises providing support plate means mounted on the radiation source having a central opening around a beam axis through which the beam of radiation can pass; a bundle of nested metal rods mounted on the support plate means each having a longitudinal axis perpendicular to the beam axis and having first ends which together define a first surface for shaping the beam around the beam axis and opposite ends from the first ends; a holder means for positioning a rod shaping means adjacent the opposite ends of the rods, wherein the rod shaping means has a second surface corresponding to the first surface which defines varying positions of the first ends of the rods so that the first surface is defined and the beam is shaped by the first ends of the rods; and clamping means mounted on the support plate means for securing the rods together in the shape defined by the shaping means; providing the rod shaping means by shaping a material to conform to an outline of an x-ray image of defined area to the body to be irradiated and thereby providing the second surface of the rod shaping means; mounting the rod shaping means in the holder means with the opposite ends of the rods engaging the rod shaping means second surface to thereby define the first surface for shaping the beam in the collimator corresponding to the x-ray image; clamping the rods with the clamping means; and irradiating the defined area of an object with the shaped beam defined by the rods.

SPECIFIC DESCRIPTION

FIGS. 1 to 6 show the adjustable or variable radiation collimator 10 of the present invention. The collimator 10 shapes a beam 100 of x-rays, neutrons or the like for use with a cyclotron 101 (or an accelerator or other radiation source) to impart a beam 100 on patient's body P such as described in U.S. Pat. No. 4,507,616 or on another object.

As shown in FIGS. 1 to 5, the collimator 10 includes a support plate 11 with a ring gear 11a around the outside circumference and with an opening 11b in the center. The beam 100 is around axis a-a which is at the center of the opening 101a from the cyclotron 101. The gear 11a is rotated by a worm gear 12 on shaft 13 by motor 14. The collimator 10 is preferably mounted on the cyclotron 101 (or an accelerator or other radiation source) by means of a ring bearing 15 around the opening 11b. The worm gear 12 and ring gear 11a rotate the support plate 11 around axis a-a.

On the side of the support plate 11 opposite the ring bearing 15, bundles of parallel rods 16 are mounted preferably so that their axes b-b are perpendicular to axis a-a. There are preferably at least two (2) and up to four (4) separate sets of bundles of rods 16. The rods 16 are packed on the support plate 11 with common axis b-b by spaced apart retainers 17 and 17a and 18 and 18a. The rods 16 are held in place in retainers 17, 17a and in retainers 18 and 18a by holder bars 19 and 19a. The bars 19 and 19a are clamped onto the rods 16 by means of clamps 20 and 20a and clamps 21 and 21a which are of the over center type as shown by the dotted lines in FIG. 2. The clamps 21 and 21a are connected to base 22 and 22a mounted on support plate 11 and clamp rods 23 and 23a which are connected to clamps 21 and 21a through bars 19 and 19a.

The position of the rods 16 along axis b-b relative to axis a-a is defined by shaping members 24 and 24a with surfaces 24b and 24c against the opposite ends 16b of the rods 16 from the first ends 16a and mounted on a first U-shaped member 25 which is in turn mounted on a second U-shaped member 26 secured to support plate 11 by means of bolts 27 and wing nuts 28. The rods 16 rest on a leveling member 29 which is milled to insure that the rods 16 are perpendicular to axis a-a (or another selected angle). A set of tabs 30 secure the retainers 17, 17a and 18 and 18a to the support plate 11 by means of bolts 31.

FIG. 6 shows a table 50 with adjustable legs 51 for vertically and horizontally adjusting a surface of the table 50 supporting a horizontal patient P. In operation the collimator 10 of the beam 100 can be arbitrarily shaped to match the projected contour of the tumor area of a patient's body to within a very accurate tolerance.

The array of the small diameter rods 16 are preferably oriented perpendicular to the direction of the beam 100 along axis a-a and with the contour of the collimator surface defined by the ends 16a of the rods 16. The location of the rod ends 16a is fixed by the shaping members 24 and 24a against ends 16b which can be made of polystyrene foam and have been previously shaped such as in a conventional, poured-collimator forming system. The surfaces 24b and 24c of the polystyrene foam match the projected surfaces 16a between the cyclotron 101 or other radiation source and the tumor in patient P. Also, the shaping members 24 and 24a can be conveniently prepared with a hot wire as a knife which is mounted on a pantographic device (not shown) with a pointer moved along on x-ray film on which the physician has marked the region to be radiated. The desired radiation defining surface 24b or 24c for shaping the ends 16a of the rods 16 is cut into the polystyrene foam as the hot wire is moved around the contour on the x-ray film.

As shown in FIGS. 3 to 5, the collimator 10 can use gravity to move rods 16 to the desired position. To accomplish this, the unit or cyclotron 101 (or other accelerator or radiation source) on which the collimator 10 is mounted is first moved to a side treatment angle such that the direction of the radiation beam a-a would be horizontal if the cyclotron 101 were in operation. In this position, the support plate 11 is then turned by means of ring gear 11a and worm gear 12 to an orientation such that the array of rods 16 on the side where shaping member 24 is to be inserted are on top so that the rods drop away from the shaping member 24 when the clamps 20 are released. The next shaping member 24 is then inserted, the support plate 11 is rotated by 180°, causing the ends 16b of rods 16 to drop down against the shaping member 24, and the rods 16 are then clamped in this position in retainers 18 and 18a using the clamps 20. At this point the ends 16a of the rods 16 present a surface identical to the surface 24b of the polystyrene foam block except for the slight graininess associated with the diameter of each individual rod 16. The same operation is repeated for the rods 16 in retainers 17 and 17a and shaping member 24a and surface 24c, after which, with clamps 20, 20a, 21 and 21a secured, the radiation therapy unit can then be rotated to the orientation desired for the treatment. After the treatment, the above sequence is repeated to remove the shaping members 24 and 24a for the patient whose treatment has been completed and insert the new shaping members 24 and 24a for the next patient.

The array of rods 16 can use either hexagonal rods or circular rods 16. If the rods 16 are circular in cross-section and packed in closest form, voids remain whose area is 9% of the total cross-sectional area, but the effect of such voids can be readily compensated for by making the array of rods 16 thicker.

Rods 16 can be composed of any radiation attenuating material such as tungsten and stainless steel which are two typical excellent materials particularly for neutron beams. The clamps 20, 20a, 21 and 21a for the rods 16 requires very little motion of clamp rods 23 and 23a to shift from rods 16 which are free to move to rods 16 which are fully clamped. The ideal motion of the clamps 20, 20a, 21 and 21a is one-half of the diameter of the circular or hexagonal rods which are in use. Rods 16 in the range of 1 mm to 3 mm in diameter would be typical.

The device which moves the clamping bars 19 and 19a from clamped to unclamped can be of many forms such as small pneumatic cylinders which are particularly convenient. Many other electrical, mechanical, and hydraulic systems can also perform this function.

It may be necessary in some instances to minimize friction between rods 16 if gravity alone is used to move the rods, especially if the rods 16 are hexagonal. In this case lubricants can be used, such as silicones.

Arrangements of three bundles of rods 16 on 120° axes or even four on 90° axes can be used and have some advantage over the two bundle configuration in allowing better conformation to certain desired cross-sections and in being more adaptable to use of an inflatable sleeve device (not shown) to conform the rods to the polystyrene foam shaping means. The inflatable sleeve or sock provides pressure against the ends 16a of rods 16 to move them into position. It works best in the three and four rod 16 bundle configuration.

There is a seam 32 where ends 16a of rods 16 meet. If this presents a leakage problem it can be solved in several ways such as: zig-zagging the two shaping means where the rods 16 meet; sloping the ends 16a of the interface of the rods 16 across the incident beam path; or pushing one set of rods 16 all the way across the opening 11b in areas where they would touch.

It will be appreciated that the rods do not have to be positioned perpendicular to the beam axis. All that is necessary is that they be movable into the beam. Thus an angle of the axis of the rods to the beam axis can be between about 10° and 90°.

It will be further appreciated that various means can be used to shape the first ends of the rods to interfere with the beam axis. For instance a pattern 200 or other shaping means in the shape of the beam 100 such as shown in FIG. 7 can be used. Further various mechanical push rod means can be used to engage the opposite ends 16a and 16b and move them to define the shape of the beam 100. The mechanical means could be computerized in a manner well known to those skilled in the art.

The beam 100 can be of any kind particularly photon (e.g. x-ray) or neutron beams. Charged particle beams can be collimated with the apparatus of the present invention.

It is intended that the foregoing description be only illustrative of the present invention and that the invention be limited only by the hereinafter appended claims.

We claim:

1. A collimator apparatus for producing a cross-sectionally shaped beam of radiation from a radiation source which comprises:
   (a) support plate means having a central opening around a beam axis through which the beam of radiation can pass;
   (b) a bundle of nested rods mounted on the support plate means each rod being movable into the beam at an angle to the beam axis to interfere with the beam, the rods having first ends which together define a first surface for shaping the beam around the beam axis and opposite ends from the first ends of the rods wherein the rods are nested so that the beam can not pass between the rods;
   (c) a holder means mounting the rods so that the first surface is defined and the beam is shaped by the first ends of the rods; and
   (d) releasable clamping means mounted on the support plate means and engaging the rods between the first and second ends to secure the rods together in the shape defined by the first ends of the rods.

2. The collimator apparatus of claim 1 wherein there are two opposed bundles of rods mounted on the support plate means with the first ends opposite each other.

3. The collimator apparatus of claim 1 wherein the rods are circular in cross-section and have a diameter of between about 1 mm and 3 mm.

4. The collimator apparatus of claim 1 wherein rods have a composition for interfering with a neutron beam.

5. The collimator apparatus of claim 1 wherein the rods have a composition for interference with a photon beam.

6. A collimator apparatus for producing a cross-sectionally shaped beam of radiation from a radiation source which comprises:
   (a) support plate means having a central opening around a beam axis through which the beam of radiation can pass;
   (b) a bundle of nested metal rods mounted on the support plate means each rod having a longitudinal axis perpendicular to the beam axis and having first ends which together define a first surface for shaping the beam around the beam axis and opposite ends from the first ends wherein the rods are nested so that the beam can not pass between the rods;
   (c) a holder means mounting the rods including shaping means adjacent the opposite ends of the rods, wherein the rod shaping means has a second surface corresponding to the first surface which defines varying positions of the first ends of the rods so that the first surface is defined and the beam is shaped by the first ends of the rods; and
   (d) clamping means mounted on the support plate means for securing the rods together in the shape defined by the shaping means.

7. The collimator apparatus of claim 6 wherein there are two opposed bundles of rods mounted on the support plate means with the first ends opposite each other and with the opposed rods having parallel longitudinal axis.

8. The collimator apparatus of claim 6 wherein the rods are circular in cross-section and have a diameter of between about 1 mm and 3 mm.

9. The collimator apparatus of claim 6 wherein the metal composition of the rods is selected from the group consisting of tungsten and stainless steel.

10. The collimator apparatus of claim 6 wherein the rod shaping means is composed of polystyrene foam which is mounted on the holder.

11. The collimator apparatus of claim 6 wherein the rods have a composition for interference with a neutron or photon beam.

12. The collimator apparatus of claim 6 wherein the rods have a polygonal cross-section.

13. The collimator apparatus of claim 6 wherein the support plate means is rotatable around the beam axis by a drive means.

14. The collimator apparatus of claim 6 wherein the support plate means is circular and has a ring gear mounted around the central opening, wherein a worm gear driven by a drive means engages the ring gear to rotate the support plate means.

15. A method of producing a cross-sectionally shaped beam of radiation from a radiation source which comprises:
   (a) providing a collimator apparatus for producing a cross-sectionally shaped beam of radiation from a radiation source which comprises: support plate means having a central opening around a beam axis through which the beam of radiation can pass; a bundle of nested rods mounted on the support plate means each rod being movable into the beam at an angle to the beam axis to interfere with the beam, the rods having first ends which together define a first surface for shaping the beam around the beam axis and opposite ends from the first ends of the rods a holder means mounting the rods so that the first surface is defined and the beam is shaped by the first ends of the rods wherein the rods are nested so that the beam can not pass between the rods; and releasable clamping means mounted on the support plate means and engaging the rods between the first and second ends to secure the rods together in the shape defined by the first ends of the rods;

(b) moving the rods in the holder means to thereby define the first surface for shaping the beam in the collimator;

(c) clamping the rods with the clamping means; and (d) irradiating the defined area of an object with the shaped beam defined by the rods.

16. A method of producing a cross-sectionally shaped beam of radiation from a radiation source which comprises:

(a) providing support plate means mounted on the radiation source having a central opening around a beam axis through which the beam of radiation can pass; a bundle of nested metal rods mounted on the support plate means each rod having a longitudinal axis perpendicular to the beam axis and having first ends which together define a first surface for shaping the beam around the beam axis and opposite ends from the first ends wherein the rods are nested so that the beam can not pass between the rods; a holder means mounting the rods including shaping means adjacent the opposite ends of the rods, wherein the rod shaping means has a second surface corresponding to the first surface which defines varying positions of the first ends of the rods so that the first surface is defined and the beam is shaped by the first ends of the rods; and clamping means mounted on the support plate means for securing the rods together in the shape defined by the shaping means;

(b) providng the rod shaping means by shaping a material to conform to an outline of an x-ray image of defined area to the body to be irradiated and thereby providing the second surface of the rod shaping means;

(c) mounting the rod shaping means in the holder means with the opposite ends of the rods engaging the rod shaping means second surface to thereby define the first surface for shaping the beam in the collimator corresponding to the x-ray image;

(d) clamping the rods with the clamping means; and (e) irradiating the defined area of an object with the shaped beam defined by the rods.

17. The method of claim 16 wherein there are two opposed bundles of rods mounted on the support plate means as mirror images of each other with the first ends opposite each other and with the rods in each bundle having parallel longitudinal axis and wherein each of the bundles of rods is mounted on one of two opposed second surfaces of two opposed rod shaping means.

18. The method of claim 16 wherein the rod shaping means is composed of polystyrene foam which is cut to the shape of the beam.

19. The method of claim 16 wherein the beam is a neutron beam and wherein the rods are made from the metal selected from tungsten and stainless steel.

20. The method of claim 16 wherein the support plate means is rotated around the beam axis by a drive means.

21. The method of claim 20 wherein the support plate means has a ring gear mounted around the central opening and wherein a drive means with a worm gear meshed to the ring gear rotates the worm gear, ring gear and support plate.

22. The method of claim 16 wherein a beam selected from neutrons and photons is produced by the radiation source.

23. The method of claim 22 wherein the beam is of neutrons produced from a target irradiated with an accelerated beam of charged particles which impinge upon the target releasing the neutrons which then pass through the opening in the support plate.

24. The method of claim 16 wherein the rods each have a circular cross-section and a diameter of between about 1 and 3 mm.

25. The method of claim 16 wherein the rods have a polygonal cross-section.

26. The method of claim 16 wherein a patient is irradiated.

* * * * *